United States Patent [19]

Boyle et al.

[11] Patent Number: 5,616,238
[45] Date of Patent: Apr. 1, 1997

[54] SOLVENT EXTRACTION OF HYDROCARBON OILS PRODUCING AN INCREASED YIELD OF IMPROVED QUALITY RAFFINATE

[75] Inventors: Joseph P. Boyle, Baton Rouge, La.; Adrianus Welmers, Mendham, N.J.

[73] Assignee: Exxon Research and Engineering Company, Florham Park, N.J.

[21] Appl. No.: 567,646

[22] Filed: Dec. 5, 1995

Related U.S. Application Data

[63] Continuation-in-part of Ser. No. 247,123, May 20, 1994, abandoned.

[51] Int. Cl.$^6$ .................................................. C10G 21/20
[52] U.S. Cl. ........................... 208/314; 208/311; 208/322; 208/326; 208/335
[58] Field of Search ..................... 208/314, 317, 208/320, 323, 325–326

[56] References Cited

U.S. PATENT DOCUMENTS

| | | | |
|---|---|---|---|
| 3,843,515 | 10/1974 | MacDonald et al. | 208/326 |
| 3,912,618 | 10/1975 | Dryer | 208/87 |
| 4,018,666 | 4/1977 | Reid et al. | 208/36 |
| 4,057,491 | 11/1978 | Bushnell et al. | 208/309 |
| 4,125,458 | 11/1978 | Bushnell et al. | 208/309 |
| 4,168,226 | 9/1979 | White et al. | 208/321 |
| 4,311,583 | 1/1982 | Woodle | 208/312 |
| 4,328,092 | 5/1982 | Sequeira | 208/326 |
| 4,510,047 | 4/1985 | Thompson | 208/321 |
| 4,892,644 | 1/1990 | Choi et al. | 208/107 |
| 4,909,927 | 3/1990 | Bell | 208/326 |
| 5,039,399 | 8/1991 | Sequeira, Jr. | 208/311 |
| 5,234,597 | 8/1993 | Welmers et al. | 210/640 |
| 5,242,579 | 9/1993 | Mead et al. | 208/312 |

FOREIGN PATENT DOCUMENTS

| | | | |
|---|---|---|---|
| 944301 | 3/1974 | Canada | 196/262 |
| 950851 | 7/1974 | Canada | 196/53 |
| 0087832A1 | 9/1983 | European Pat. Off. | C10G 21/00 |
| 0430444A1 | 6/1991 | European Pat. Off. | C10G 21/00 |
| 2595371 | 8/1987 | France | C10G 53/06 |
| 2595370 | 9/1987 | France | C10G 21/28 |
| 1556003 | 11/1979 | Great Britain . | |

*Primary Examiner*—Helane Myers
*Attorney, Agent, or Firm*—Joseph J. Allocca; James H. Takemoto

[57] ABSTRACT

The present invention is directed to an improved selective solvent extraction process wherein a hydrocarbon feed stream containing a mixture of aromatics and non-aromatics is contacted with an aromatics selective solvent in an extraction zone to produce an aromatics rich extract phase and an aromatics lean raffinate phase, water in a carefully controlled amount is added to the recovered extract phase resulting in the separation of the extract phase into a hydrocarbon rich pseudo-raffinate which is recycled to the extraction zone for processing with fresh feed and an increased yield of raffinate of higher quality than is obtained without pseudo-raffinate recycle.

7 Claims, 2 Drawing Sheets

RAFFINATE QUALITY USING EXTRACT SOLUTION WATER INJECTION TO GENERATE RECYCLE

RAFFINATE YIELD USING EXTRACT SOLUTION WATER INJECTION TO GENERATE RECYCLE

RAFFINATE QUALITY USING EXTRACT SOLUTION WATER INJECTION AND CHILLING

RAFFINATE YIELD USING EXTRACT SOLUTION WATER INJECTION AND CHILLING 5,616,238

SOLVENT EXTRACTION OF HYDROCARBON OILS PRODUCING AN INCREASED YIELD OF IMPROVED QUALITY RAFFINATE

This application is a continuation-in-part of U.S. Ser. No. 08/247,123, filed May 20, 1994 now abandoned.

BACKGROUND OF THE INVENTION

1. Field of the Invention

This invention relates to the selective extraction of aromatic hydrocarbons from a bed stream comprising a mixture of aromatic and non-aromatic hydrocarbons by use of a selective extraction solvent and to the improvement of that process so as to produce increased yields of improved quality product.

2. Description of the Related Art

The separation of aromatics from hydrocarbon feed streams comprising mixtures of aromatics and non-aromatics by solvent extraction is a process which has long been practiced in the refining industry especially in the production of lubricating oil. The process involves the use of solvents such as phenol, furfural, n-methyl pyrrolidone which are selective for the aromatic components present in the hydrocarbon feed streams. The hydrocarbon stream and the selective solvents are combined, typically and preferably under counter-current conditions. The contacting results in concentration of the aromatic component in the selective solvent. Because the solvent and the hydrocarbon oil are of different densities and generally immiscible after the contacting, the aromatics rich solvent phase separates from the mixture thereby resulting in an aromatics rich solvent phase, called the extract, and an aromatics lean non-aromatics rich product phase called the raffinate. Because no solvent extraction process can be one hundred percent selective, the aromatics rich extract phase contains a minor but economically significant quantity of non-aromatic hydrocarbon which constitute good lube oil molecules.

Processes designed to recover these good lube oil molecules present in the extract phase have been proposed and disclosed in the literature.

U.S. Pat. No. 5,242,579 teaches a control method for solvent refining lube oils. The process disclosed consists of a solvent extraction zone wherein feed and solvent are contacted countercurrently. The primary extract is separated into a secondary raffinate and a secondary extract by cooling the primary extract 10° F. to 120° F. below the extraction temperature. The addition of an anti-solvent to the primary extract in combination with at least 10° F. cooling is optional. Secondary raffinate is passed to the extraction zone with the fresh feed.

U.S. Pat. No. 4,328,092 teaches the solvent extraction of hydrocarbon oils. The process uses N-methyl-2-pyrrolidone. The extract from the solvent extraction zone is cooled to form two immiscible liquid phases, a secondary extract phase and a secondary raffinate phase. The secondary raffinate phase is recycled to the extraction zone resulting in increased yield of refined oil product and in energy savings.

U.S. Pat. No. 4,311,583 teaches a solvent extraction process. A hydrocarbon feed is contacted with N-methyl pyrrolidone in an extraction zone. The primary extract is separated into a secondary raffinate and a secondary extract by cooling the primary extract optionally with the addition of water or wet solvent. The secondary raffinate is separated from the secondary extract. At least part of the secondary raffinate is combined with the raffinate to obtain an increased yield of desired quality raffinate oil product. As part of the secondary raffinate may be returned to the lower part of the extraction zone.

French Patent 2,595,371 teaches a process for the selective solvent extraction of a hydrocarbon mixture. Solvent is passed counter-currently to the hydrocarbon feed employing 2 or more separation columns resulting in the separation of the feed into a raffinate, a pseudo-raffinate and an extract. Feed is introduced into a first column while fresh solvent is introduced into the top of a second column. The overheads from the first column constitute the feed to the second column. The bottoms from the second column are cooled and permitted to salt-out in a separation zone wherein an upper phase pseudo raffinate is recovered and a bottom phase of recycle solvent is recovered. This bottom phase recycle solvent is used as the solvent introduced into the first column. Extract is recovered from the bottom of the first column and raffinate from the top of the second column. In an alternative embodiment part of the pseudo raffinate can be cycled back to the bottom of the second column while the extract from the first column can be cooled to salt-out in a separation zone producing an upper phase of lighter hydrocarbon which is recycled to the bottom of the first column, and a true extract bottoms phase.

French Patent 2,595,370 teaches a multiple effect extraction process using counter-current solvent flow. The process utilizes a main column separated into 2 zones by a draw-off tray and a second column which fractionates the side stream drawn off from the first column. The fractionation zone produces an overhead raffinate which is fed back to the top zone of column 1 above the draw-off tray. The bottoms from the fractionation zone are cooled and separated into a pseudo raffinate and an extract. This extract is recycled to the bottom zone of column 1 just below the draw-off tray. It can optionally also be fed into the top zone of column 1 just above the draw-off tray. By this scheme a raffinate is recovered from the top of the first column, an extract from the bottom of said column and a pseudo raffinate from the separation zone to which the bottoms fraction from the fractionation zone is fed.

In an alternate embodiment the extract from the bottom of column 1 can be cooled to salt-out in a separation zone an upper phase of lighter hydrocarbons which is recycled back to the bottom of the bottom zone of column 1. The bottoms fraction from this separation zone is a true extract phase.

Figure 1A:
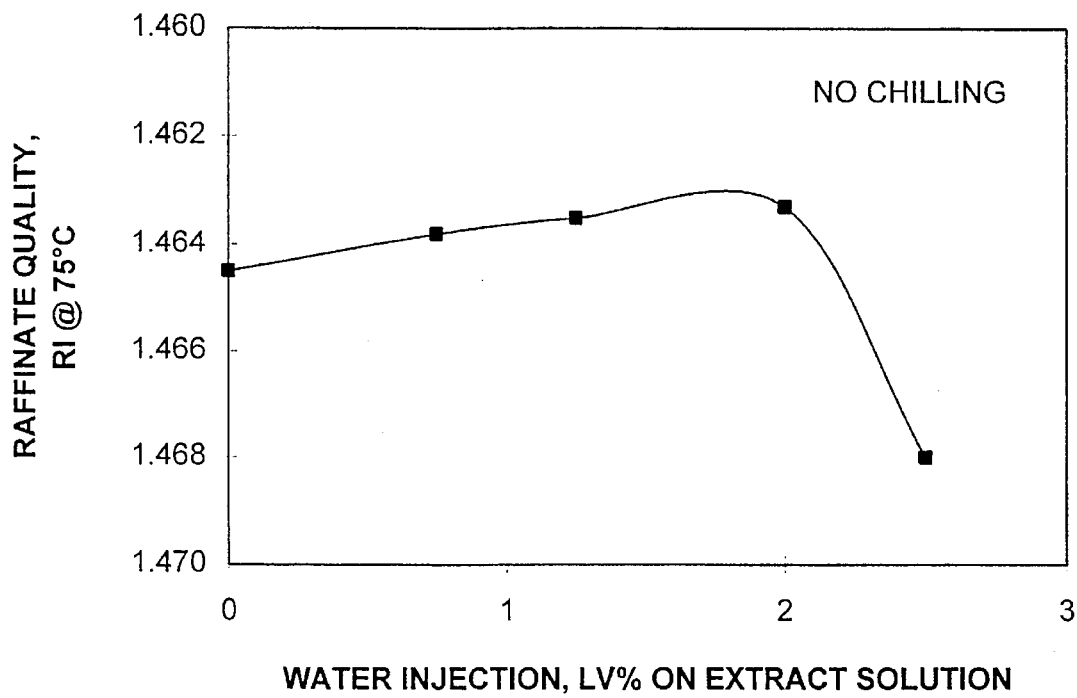
FIGS. 1A and 1B present the relationship which exists between the amount of water injected (of extract solution) and yield and the resultant quality of the raffinate produced.

The solvent extraction process comprises contacting the hydrocarbon feed stream with a selective extraction solvent. The selective extraction solvent can be any solvent known to have an affinity for aromatic hydrocarbons in preference to non-aromatic hydrocarbons. Examples of such solvents include, sulfolane, furfural, phenol, N-methyl pyrrolidone (NMP). The solvent may contain from 0 to 50 LV % water, preferably 0 to 20 LV % water. When the solvent used is NMP, it may contain 0 to 10 LV % water, preferably 1 to 5 LV % water.

Contacting of the selective extraction solvent with the hydrocarbon feed may be conducted using any typical technique common to the industry such as batch contacting or counter-current contacting, preferably counter-current contacting.

Counter-current contacting is conducted in an elongated treating zone or tower, usually vertical. The hydrocarbon feed to be extracted is introduced at one end of the tower while the selective solvent is introduced at the other. To facilitate separation of the materials in the tower the less dense material is introduced near the bottom of the tower while the more dense material is introduced near the top. In this way the solvent and hydrocarbon are forced to pass counter-currently to each other in the tower while migrating to the end opposite that of their introduction in response to their respective densities. In the cause of such migration the aromatic hydrocarbons are absorbed into the selective solvent.

When using NMP, the solvent is introduced near the top of the tower while the hydrocarbon feed is introduced near the bottom. In that embodiment the hydrocarbon is introduced into the tower at a temperature in the range 0° to 200° C., preferably 50 to 150° C., while the NMP, introduced into the top of the tower is at a temperature in the range 0° to 200° C., preferably about 50° C. to 150° C.

Counter-current extraction using NMP is typically conducted under conditions such that there is a temperature differential between the top and bottom of the tower of at least about 10° C., preferably at least 40° C., most preferably about 50° C.

Overall tower temperature is below the temperature of complete miscibility of oil in solvent.

The extraction solvent, preferably NMP, is added in a amount within the range of 50 to 500 LV % solvent, preferably 100–300 LV %, most preferably 100 to 250 LV % solvent based on fresh feed.

Water injection to the aromatics rich solvent extract takes place in the absence of any external cooling. The small volumes of water injected into the solvent extract do not result in any appreciable cooling of the extract. Such incidental cooling is less than 10° F, normally less than 5° F. It is preferred that water injected be pre-heated for example, water stripped from warm solvent. While cooling may aid in phase separation, it suffers from energy debits. Energy is required to chill the solvent extract. In addition, recycle of the cooled raffinate from phase separation may require heating to minimize upset of operating conditions of the extraction unit itself. Furthermore, in the case of heavy, waxy feeds, cooling may cause any waxy paraffins in the extract phase to separate out as a solid thereby leading to potential plugging problems. Other drawbacks of cooling are the additional capital investment in the chiller and solvent inventory.

The amount of pseudo raffinate recycled to the extraction process for re-extraction in combination with the fresh feed may be in the range of about 0.01 to 0.9 volumes of pseudo raffinate per volume fresh feed, most preferably 0.01 to 0.7 volumes of recycle per volume fresh feed, most preferably 0.05 to 0.4 volumes of recycle per volume fresh feed.

The pseudo raffinate recycle is introduced into the extraction tower at any point below that at which the extraction solvent is introduced, preferably in the vicinity of the point of introduction of the fresh feed, most preferably above the point of introduction of the fresh feed or in admixture with the fresh feed.

By practice of the present invention an increased yield of raffinate product is produced. This raffinate is as of high or higher quality, as evidenced by a lower Refractive Index (RI), than the raffinate produced without pseudo raffinate recycle, and without resort to increasing the ratio of solvent treat to total charge.

EXAMPLE 1

Commercial countercurrent extraction was simulated in a laboratory counter current extractor which was coupled to an outboard settler. In this test both the tower and settler were operated at 95° C. and water was injected upstream of the settler in the range 0.7–2.5 LV % on the extract solution, i.e. extract oil plus solvent leaving the bottom of the extractor.

In the base case experiment, a 600N Gulf Coast distillate having a density of 0.9352 and a refractive index of 1.5003 at 75° C. was fed to a laboratory extractor where it was contacted with NMP containing 2.3% water at a treat ratio of 190 LV % and 95° C. The yield of raffinate was 50.4 LV % on fresh feed with a refractive index at 75° C. of 1.4647. These results are given in Table 1 along with experiments in which water was injected upstream of an outboard settler. The settler was also at 95° C. and the separated pseudo-raffinate was recycled with the distillate. The refractive index and density of the separated pseudo-raffinates were lower than (i.e., better than) those of the feed for experiments A, B and C corresponding to injection of water at 0.7 LV %, 1.3 LV % and 1.9 LV % on extract solution. It is shown in Table 1 that the yield on fresh feed increases with water injection while the treat to total charge ratio is kept at 190 LV %. It is observed that the quality of the raffinate recovered from the recycle operation is better than the base case by as much as 0.0018 units of RI @75° C.

Experiment D shows results obtained with 2.5 LV % water injected into the extract solution. In this case, the operation appeared less stable and the quality of the pseudo-raffinate was worse than that of the fresh distillate feed. While the yield of raffinate showed an increase, the quality in terms of RI @75° C. was worse (0.0035 higher) than the base case.

Figure 1B:
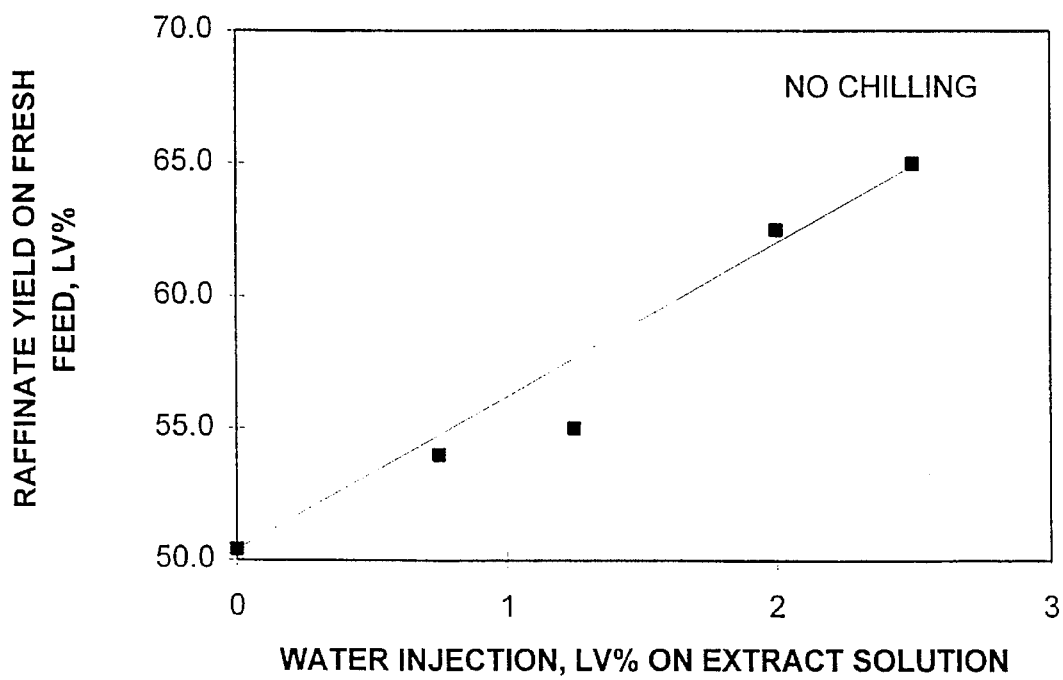
Figure 2A:
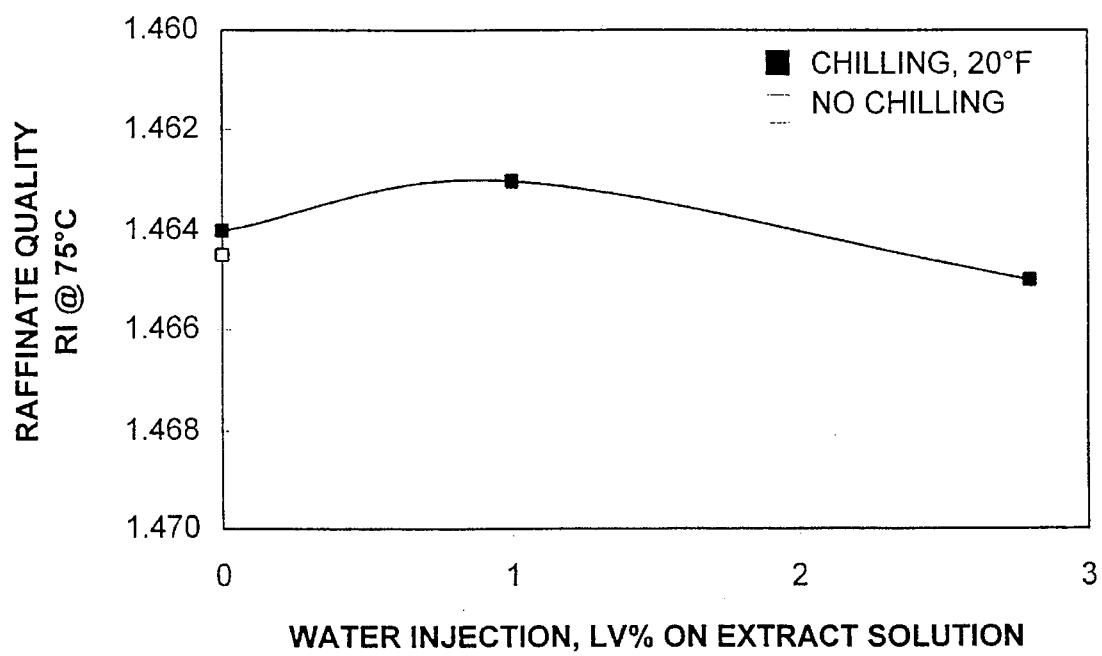
FIGS. 2A and 2B present the relationship which exists between the amount of water injection (on extract solution) and yield and the resultant quality of the raffinate produced when water injection is used in combination with extract solution cooling. DESCRIPTION OF THE INVENTION It has been discovered that the solvent extraction of hydrocarbon feed streams comprising mixtures of aromatic and non-aromatic hydrocarbons by using an aromatics selective extraction solvent contacted with the hydrocarbon feed in an extraction zone to produce an aromatics lean raffinate product stream and an aromatics rich solvent extract stream is improved by subjecting the aromatics rich solvent extract stream to a water injection step in the absence of external cooling to produce a phase separation resulting in the generation of a hydrocarbon rich pseudo-raffinate phase. This pseudo raffinate phase is recycled to the extraction zone for re-extraction therein in combination with the feed without any increase in the solvent treat to charge ratio. The water injection step utilized from 0.1 to 5.0 LV % water, based on the amount of extract solution being processed, preferably 0.1 to 2.5 LV % water, most preferably 1 to 2.5 LV % water, the higher quantities of water additive being employed when lower efficiency extraction towers are being used. The recycle of pseudo-raffinate produced by using such volumes of added water results in the production of an increased volume of raffinate products having a quality higher than that of the raffinate produced under the same conditions at the same extraction solvent treat ratio but without pseudo-raffinate recycle.
Figure 2B:
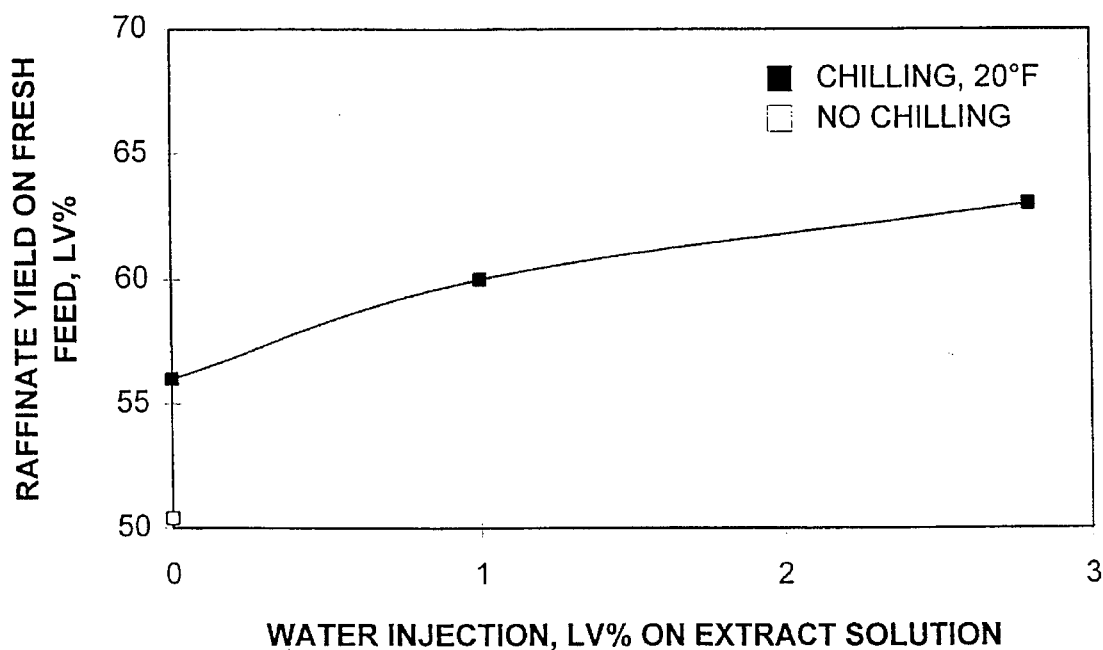

Results of the 5 experiments are also shown in FIG. 1. Water injection up to 2 LV % on extract solution results in a significant yield increase on fresh feed without increasing the ratio of treat to total charge. In addition, the raffinate quality is superior. Because in this case the extract solution is coming from a relatively high efficiency extraction tower, above 2 LV % water injection on extract solution, operation of the treater was unstable, and although yield of raffinate was somewhat higher, its quality showed a large deterioration 0.0052 RI @75° C. higher than the 2 LV % water case of Experiment C.

TABLE 1

| Experiment Number | Base | ← Water Injection → | | | |
|---|---|---|---|---|---|
| | | A | B | C | D |
| Fresh Feed Rate, ccs/min | | ← 10.5 → | | | |
| RI @ 75° C. | | ← 1.5003 → | | | |
| Density @ 15° C. | | ← 0.9352 → | | | |
| Temperatures, °C. | | | | | |
| Tower | 95 | ← 95 → | | | |
| Settler | none | ← 95 → | | | |
| Water Injected | | | | | |
| LV % on Extract Solution | nil | 0.7 | 1.3 | 1.9 | 2.5 |
| Sprung Pseudo-raffinate, ccs/min | nil | 1 | 2 | 4 | 5 unstable |
| RI @ 75° C. | — | 1.4870 | 1.4902 | 1.4949 | 1.5057 |
| Density @ 15° C. | — | 0.9191 | 0.9238 | 0.9313 | 0.9424 |
| Total Charge, ccs/min | 10.5 | 11.5 | 12.5 | 14.5 | 15.5 |
| Treat Solvent, NMP | | | | | |
| % Water | | ← 2.3 → | | | |
| Ratio to Total Charge, LV % | | ← 190 → | | | |
| Rate, ccs/min | 20 | 21.8 | 23.7 | 27.5 | 29.5 |
| Raffinate | | | | | |
| Rate, ccs/min | 5.3 | 5.6 | 5.9 | 6.6 | 6.8 |
| LV % on Fresh Feed | 50.4 | 53.6 | 56.3 | 62.5 | 64.8 |
| RI @ 75° C. | 1.4647 | 1.4633 | 1.4629 | 1.4630 | 1.4682 |
| Density @ 15° C. | 0.8843 | 0.8831 | 0.8826 | 0.8829 | 0.8876 |

EXAMPLE 2

The feed quality and mode of operation are similar to Example 1. However, in Experiment E, the extraction solution is cooled 20° C. and in experiments F and G water is injected to the extract solution in combination with cooling. The ratio of treat to total charge was maintained at 190 LV % and the solvent water content was maintained at 2.3%.

Results are given in Table 2. Experiment E shows that the raffinate yield is increased from 50.4 LV % by chilling and recycling the separated pseudo-raffinate as has been demonstrated in prior art. Unexpectedly, a substantial further increase in yield can be obtained by injection of 1.1 LV % water on the extraction solution. In addition to the raffinate yield increase, quality is 0.0013 units of RI better than E.

As in Experiment D, Example 1, in Experiment G a high amount of water was injected and the yield of raffinate increased further. However, at this level, the operation was unstable and the quality of the pseudo-raffinate recycle and raffinate oil inferior to the base case and the other experiments E and F as implied by RI.

These results are illustrated in Table 2.

TABLE 2

| Experiment Number | Base | Chilling | ← Chill + H₂O Inj. → | |
|---|---|---|---|---|
| | | E | F | G |
| Fresh Feed Rate, ccs/min | | ← 10.6 → | | |
| RI @ 75° C. | | ← 1.5003 → | | |
| Density @ 15° C. | | ← 0.9352 → | | |
| Temperatures, °C. | | | | |
| Tower | | ← 95 → | | |
| Settler | none | ← 75 → | | |
| Water Injected | | | | |
| LV % on Extract Solution | nil | nil | 1.1 | 2.6 |
| Sprung Pseudo-raffinate, ccs/min | nil | 1.3 | 3.8 | 5.2 |
| RI @ 75° C. | — | 1.4884 | 1.4923 | 1.5102 |
| Density @ 15° C. | — | 0.9215 | 0.9274 | 0.9364 |
| Total Charge, ccs/min | 10.5 | 11.8 | 14.2 | 15.2 |
| Treat Solvent, NMP | | | | |
| % Water | | ← 2.3 → | | |
| Ratio to Total Charge, LV % | | ← 290 → | | |
| Rate, ccs/min | 20 | 22.5 | 27 | 29 |
| Raffinate | | | | |
| Rate, ccs/min | | | | |
| LV % on Fresh Feed | 50.4 | 55.5 | 60.0 | 62.3 |
| RI @ 75° C. | 1.4647 | 1.4643 | 1.4630 | 1.4653 |
| Density @ 15° C. | 0.8843 | 0.8847 | 0.8831 | 0.8865 |

EXAMPLE 3

The feed quality and mode of operation are similar to Example 1. However, instead of the extractor being operated isothermally, a temperature gradient of 40° C. is imposed which, in itself, increases raffinate yield. this is shown in Experiment H.

In the operation of this tower, further increases of the temperature gradient above 40° C. did not provide further yield increases. Rather the operation appear unstable, exhibiting a throughput capacity limitation, flooding.

However if water injection is superimposed on an external already providing an increased yield by means of a thermal gradient a substantially higher yield can be achieved. This is shown in experiment J.

TABLE 3

| Experiment Number | Base | Gradient H | Gradient + H₂O Inj. J |
|---|---|---|---|
| Fresh Feed Rate, ccs/min | | ← 10.6 → | |
| RI @ 75° C. | | ← 1.5003 → | |
| Density @ 15° C. | | ← 0.9352 → | |
| Temperatures, °C. | | | |
| Tower Top | 95 | 115 | 115 |
| Tower Bottom | 95 | 75 | 75 |
| Settler | 95 | 75 | 75 |
| Water Injected | | | |
| LV % on Extract Solution | nil | nil | 1.5 |
| Sprung Pseudo-raffinate, ccs/min | nil | nil | 0.8 |
| RI @ 75° C. | | | 1.4953 |
| Density @ 15° C. | | | 0.9392 |
| Total Charge, ccs/min | 10.6 | 10.6 | 11.4 |

TABLE 3-continued

| Experiment Number | Base | Gradient H | Gradient + H$_2$O Inj. J |
|---|---|---|---|
| Treat Solvent, NMP | | | |
| % Water | 2.3 | 2.3 | 2.3 |
| Ratio to Total Charge, LV % | 190 | 190 | 190 |
| Rate, ccs/min | 20 | 20 | 21.7 |
| Raffinate | | | |
| Rate, ccs/min | 5.3 | 6.1 | 6.6 |
| LV % on Fresh Feed | 50.4 | 58.1 | 62.0 |
| RI @ 75° C. | 1.4647 | 1.4644 | 1.4634 |
| Density @ 15° C. | 0.8843 | 0.8855 | 0.8835 |

From the above it is seen that in order to achieve a yield increase from a base case of 50.4 LV % to 55.5 LV %, one can chill the extract solution by 20° C. To obtain an equivalent yield utilizing water injection alone would require injection of 0.8 LV % water (on an extraction solution) into the extraction solution. The main operating cost of either process is energy required, in the case of chilling, to reheat the extract solution and, in the case of water injection, to vaporize the injected water from the solvent downstream.

For every 100 barrels of fresh feed processed, the amount of sensible heat lost in cooling 20° C. is estimated to be 1.433M BTU's.

For vaporization of the incremental water injected per 100 barrels of fresh feed, the energy required is estimated to be 0.63M BTU's.

This energy cost associated with water injection is less than 50% of those of chilling for equivalent raffinate yield improvement of 5 LV % on fresh feed. Expresses as BTU/barrel of incremental raffinate we obtain:

Chilling: 286 k BTU/barrel

Water Injection: 126 k BTU/barrel

Thus, water injection can be used to produce a pseudo raffinate which, when added to the fresh feed results in the production of an increased yield of a higher quality product as compared to the non-recycle, straight run case, and at a lower cost as compared to similar results obtained by using pseudo raffinate produced solely by cooling.

EXAMPLE 4

Water injection tests were conducted in a commercial extraction unit using 150N and 350N feedstocks. A fresh 150N feed (refractive index of 1.4820 @75° C.) was injected at the bottom of a commercial countercurrent extractor containing phenol as the extraction solvent. An aromatics rich extract was removed from the bottom of the extraction unit and water from a solvent stripping unit was injected into aromatics rich extract stream. The combined water/extract stream was conducted to a settler where a lighter pseudo-raffinate phase was removed and recycled to the extraction unit. The extraction unit and settling unit were run at 70° C. The results are shown in Table 4.

TABLE 4

| | Base | 1 | 2 |
|---|---|---|---|
| Fresh Feed, kL/hr. | 34 | 34 | 34 |
| Water Injected | 0 | 1.5 | 2.3 |
| Treat Ratio solvent/fresh feed | 1.4 | 1.4 | 1.4 |
| Raffinate yield kL/hr. | 22.7 | 23.5 | 23.8 |

This example demonstrates that at a constant fresh feed rate and treat ratio, the quantity of raffinate could be increased by about 4% without increasing the solvent treat ratio. This results in a significant yield credit of raffinate which in turn increases the yield of lubricating oil basestock for a given charge of fresh feed.

What is claimed is:

1. An improved method for the solvent extraction of hydrocarbon feed streams comprising mixtures of aromatic and non-aromatic hydrocarbons using an aromatics selective extracting solvent wherein the hydrocarbon feed is contacted with the selective solvent in an extraction zone to produce an aromatics lean raffinate product stream and an aromatics rich solvent extract solution stream wherein the improvement comprises subjecting the aromatics rich solvent extract stream to a water injection step in the absence of external cooling to produce a phase separation resulting in the generation of a hydrocarbon rich pseudo-raffinate phase, recycling the pseudo-raffinate phase to the extraction zone for re-extraction therein in combination with fresh feed without any increase in the solvent treat to charge ratio thereby producing increased volumes of raffinate product having a quality higher than that produced under the same conditions at the same extraction solvent treat rate but without pseudo raffinate recycle, the water injection step using from 0.1 to 5.0 LV % water based on the amount of extract solution being processed.

2. The process of claim 1 wherein the water springing step utilizes from 0.1 to 2.5 LV % water based on the amount of extract solution being processed.

3. The process of claim 1 wherein the water springing step utilizes from 1.0 to 2.5 LV % water based the amount of extract solution being processed.

4. The process of claim 1 wherein the extraction solvent is selected from Sulfolane, phenol, furfural, N-methyl-pyrrolidone.

5. The process of claim 4 wherein the extraction solvent contains from 0 to 50 LV % water.

6. The process of claim 1 wherein the extraction solvent is used in an amount in the range 50 to 500 LV % solvent based on fresh feed.

7. The process of claim 1 wherein the amount of pseudo-raffinate recycled to the extraction process is in the range 0.01 to 0.9 volumes of pseudo raffinate per volume of fresh feed.

* * * * *